United States Patent
Akiyama et al.

(10) Patent No.: US 9,899,198 B2
(45) Date of Patent: Feb. 20, 2018

(54) METHOD FOR ANALYZING EVOLVED GAS AND EVOLVED GAS ANALYZER

(71) Applicant: HITACHI HIGH-TECH SCIENCE CORPORATION, Tokyo (JP)

(72) Inventors: Hideyuki Akiyama, Tokyo (JP); Kentaro Yamada, Tokyo (JP); Masafumi Watanabe, Tokyo (JP); Toshitada Takeuchi, Tokyo (JP); Kantaro Maruoka, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 0 days.

(21) Appl. No.: 15/356,581

(22) Filed: Nov. 19, 2016

(65) Prior Publication Data

US 2017/0148617 A1 May 25, 2017

(30) Foreign Application Priority Data

Nov. 20, 2015 (JP) .................. 2015-227370
Nov. 20, 2015 (JP) .................. 2015-227371
Sep. 6, 2016 (JP) .................. 2016-173394

(51) Int. Cl.
*H01J 49/10* (2006.01)
*H01J 49/04* (2006.01)
(Continued)

(52) U.S. Cl.
CPC ...... *H01J 49/0422* (2013.01); *G01N 30/7206* (2013.01); *H01J 49/0409* (2013.01); *H01J 49/10* (2013.01)

(58) Field of Classification Search
CPC ...... G01N 27/624; G01N 27/622; G01N 1/38; G01N 30/7253; G01N 30/30; G01N 30/32;
(Continued)

(56) References Cited

U.S. PATENT DOCUMENTS 4,814,612 A * 3/1989 Vestal .............. G01N 30/7253
250/282
4,883,958 A * 11/1989 Vestal .............. G01N 30/7273
250/281
(Continued)

FOREIGN PATENT DOCUMENTS

JP    2005-106524 A    4/2005
JP    2008-190898 A    8/2008

*Primary Examiner* — David A Vanore
(74) *Attorney, Agent, or Firm* — Maschoff Brennan

(57) ABSTRACT

Disclosed herein is a method for analyzing evolved gas and an evolved gas analyzer, the method correcting detection sensitivity differences in analysis devices, day-to-day variations thereof, thereby quantifying a measurement target with high accuracy. The method for analyzing evolved gas of the apparatus including: a sample holder; a heating unit evolving a gas component; an ion source generating ions by ionizing the gas component; a mass spectrometer detecting the gas component; and a gas channel through which mixed gas flows, the method including: operating a discharged flow rate controlling process of controlling a flow rate of the mixed gas discharged to outside; operating a sample holder cooling process of cooling the sample holder by bringing the sample holder into contact with a cooling unit; and operating a correction process including: correcting a mass spectrum position; calculating a sensitivity correction factor; and calculating a heating correction factor.

5 Claims, 12 Drawing Sheets

(51) Int. Cl.
*G01N 25/00* (2006.01)
*G01N 27/62* (2006.01)
*G01N 30/72* (2006.01)

(58) Field of Classification Search
CPC ........... G01N 30/7213; G01N 30/7273; G01N 30/7286; G01N 30/7293; H01J 49/049; H01J 49/105; H01J 49/0495; H01J 49/0486; H01J 49/0422; H01J 49/0409; H01J 49/0445; H01J 49/04; H01J 49/022; H01J 37/08
USPC .... 250/288, 282, 287, 281, 423 R, 424, 425
See application file for complete search history.

(56) References Cited

U.S. PATENT DOCUMENTS

| | | | | |
|---|---|---|---|---|
| 5,367,163 | A * | 11/1994 | Otsuka | H01J 49/105 250/281 |
| 7,928,370 | B2 * | 4/2011 | Amirav | H01J 49/049 250/281 |
| 2006/0192103 | A1 * | 8/2006 | Landgraf | G01N 27/624 250/287 |
| 2008/0128615 | A1 * | 6/2008 | Yamada | H01J 49/0422 250/288 |
| 2012/0326022 | A1 * | 12/2012 | Kumano | H01J 49/0495 250/282 |
| 2013/0277547 | A1 * | 10/2013 | Sato | G01N 27/624 250/282 |
| 2017/0146497 | A1 * | 5/2017 | Akiyama | G01N 33/0006 |
| 2017/0146503 | A1 * | 5/2017 | Akiyama | G01N 33/0016 |
| 2017/0148616 | A1 * | 5/2017 | Akiyama | H01J 49/0422 |
| 2017/0148617 | A1 * | 5/2017 | Akiyama | H01J 49/0422 |

\* cited by examiner

METHOD FOR ANALYZING EVOLVED GAS AND EVOLVED GAS ANALYZER

CROSS REFERENCE TO RELATED APPLICATION(S)

This application claims the benefit of Japanese Patent Application No. 2015-227370, filed Nov. 20, 2015, and Japanese Patent Application No. 2015-227371, filed Nov. 20, 2015, and Japanese Patent Application No. 2016-173394, filed Sep. 6, 2016, which are hereby incorporated by reference in their entirety into this application.

BACKGROUND OF THE INVENTION

1. Technical Field

The present invention relates generally to a method for analyzing evolved gas and an evolved gas analyzer, the method analyzing gas components evolved by heating a sample, thereby identifying, quantifying, etc. the sample.

2. Description of the Related Art

In order to increase flexibility of resins, plasticizers such as phtalates, etc. are added to the resins. After 2019, four substances of the phtalates will be restricted under the restriction of hazardous substances directive (RoHS). Therefore, it is required to identify and quantify the phtalates in the resins.

The phtalates are volatile substances such that a conventional evolved gas analysis (EGA) is applied to analyze the phtalates. The EGA is a method used to analyze gas components evolved by heating a sample by using a gas chromatograph or using various analyzers applying mass spectrometry, etc.

However, mass spectrometry is highly sensitive such that detection accuracy is high. Therefore, it is required to precisely correct the sensitivity, etc. In addition, a mass spectrometer is a general-purpose analysis device. Therefore, it is required for a user to perform complicated operations such as a sensitivity adjustment or a correction depending on a measurement target.

Therefore, technology of correcting a mass-to-charge ratio m/z (mass number) of the measurement target by using a mass spectrum of a reference sample is disclosed in Patent Documents 1 and 2.

DOCUMENTS OF RELATED ART (Patent Document 1) Japanese Patent Application Publication No. 2008-190898
(Patent Document 2) Japanese Patent Application Publication No. 2005-106524

SUMMARY OF THE INVENTION

As shown in FIG. 13, a gas component, which is a measurement target, is quantified based on an area S of a chromatogram C. Therefore, it is required to correct or adjust the chromatogram C. The area S of the chromatogram C is influenced by a measured temperature, degradation of an ion source ionizing a gas component, etc. In addition, a shape of the chromatogram (time t indicating a maximum peak of the chromatogram) is influenced by a heating rate (temperature rising rate) of a sample. When the shape of the chromatogram C changes into a chromatogram C', time t changes into time t', and the area S changes into an area S' of the chromatogram C'.

The correction and the adjustment may be performed according to an instruction manual of an analysis device. However, a general correction is not always optimized for analyzing each measurement target. Therefore, an additional correction or adjustment may be required depending on the measurement target. In order to perform the correction and adjustment, professional knowledge or experience, and proper reference substances are required. Consequently, operations are complicated, and thus work efficiency is reduced.

In an evolved gas analysis, a sample is placed on a sample stage, and the sample is heated by the sample stage in a heating furnace. Alternatively, the sample is set on a holding tool, and the holding tool is inserted into the heating furnace to evolve a gas component for the analysis. In addition, after the analysis, the sample stage is naturally cooled to a room temperature, and the sample is changed and is heated from about the room temperature to start a next analysis. However, standby time to cool the sample stage is long, and thus, work efficiency of the entire analysis process is reduced.

In addition, in the evolved gas analysis, the evolved gas component flows with carrier gas such as nitrogen gas, etc. so as to be introduced into a detecting unit. However, when a plurality of gas components are evolved, gas density is too high. Therefore, the gas density exceeds a detection range of a detecting device and thus, the detection signal is overly scaled, whereby the measurement is inaccurate.

In addition, when using a mass spectrometer as the detecting device, the gas component is ionized at the front thereof. However, in case of the gas component including an accessory substance, which is not the measurement target, when a plurality of gas components are evolved, a plurality of accessory substances are also ionized. Therefore, substances of the measurement targets are insufficiently ionized, and thus, the detection signal of the measurement target is degraded (ion-suppression).

Accordingly, the present invention has been made keeping in mind the above problems occurring in the related art, and an object of the present invention is to provide a method for analyzing evolved gas and an evolved gas analyzer, the method easily correcting detection sensitivity differences in analysis devices, day-to-day variations thereof, etc., thereby quantifying a measurement target with high accuracy.

In order to accomplish the above object, the present invention provides a method for analyzing evolved gas of an evolved gas analyzer including: a sample holder holding a sample; a heating unit receiving the sample holder therein, and evolving a gas component by heating the sample; an ion source generating ions by ionizing the gas component evolved by the heating unit; a mass spectrometer detecting the gas component by applying mass spectrometry to the ions; and a gas channel connecting the heating unit to the mass spectrometer, the gas channel through which mixed gas of the gas component and carrier gas carrying the gas component to the mass spectrometer flows, the method including: operating a discharged flow rate controlling process of controlling a flow rate of the mixed gas discharged to an outside of a branching channel based on a detection signal received from the mass spectrometer so as to control the detection signal to be within a predetermined range; operating a sample holder cooling process of cooling the sample holder by bringing the sample holder into direct or indirect contact with a cooling unit provided at an outside of the heating unit, when the sample holder is moved to a discharging position at which the sample is supplied on or removed from the sample holder; and operating a correction process by using a reference sample including the gas component as a measurement target, the correction process including: correcting a mass spectrum position (m/z value) to be located at a reference spectrum position, the mass spectrum position corresponding to a mass-to-charge ratio m/z of a mass spectrum of the gas component of the reference sample; after the correcting of the mass spectrum position (m/z value), calculating a sensitivity correction factor $Cs=Ss/S$ by using an area S and a reference area Ss of a chromatogram showing an intensity of the gas component of the reference sample at a retention time, the sensitivity correction factor being used to measure an area of a chromatogram of the gas component of a test sample; and calculating a heating correction factor $H=t/ts$ by using a time t and a reference time ts indicating a maximum peak of the chromatogram of the gas component of the reference sample, the heating correction factor being used to correct a heating rate of the test sample in the heating unit, when measuring the gas component of the test sample.

According to the evolved gas analyzer, the sample holder is in contact with the cooling unit to cool the sample holder. Therefore, in comparison with natural cooling, the sample holder is rapidly cooled, and thus, analysis work efficiency is enhanced. In addition, for example, it is possible to measure a plurality of samples for quality management, etc. Furthermore, the sample holder is cooled at an outside of the heating unit such that the cooling unit is not exposed to high temperature air of the heating unit. Therefore, excessive cooling performance is unnecessary, and the cooling unit or the entire apparatus may be provided in a small size. In addition, air temperature in the heating unit is not reduced by cooling such that extra energy and time is unnecessary to heat the heating unit again.

In addition, it is unnecessary to provide the cooling unit in the heating unit, whereby the heating unit or the entire apparatus may be provided in a small size.

Furthermore, when the gas density is too high due to the plurality of evolved gas components, a flow rate of the mixed gas discharged from the branching channel to the outside is increased, and a flow rate of the mixed gas introduced from the gas channel into the detecting device is decreased. Therefore, it is possible to avoid that the gas density exceeds the detection range of the detecting device and thus, the detection signal is overly scaled, whereby the measurement is inaccurate.

Here, the flow rate of the mixed gas discharged from the branching channel to the outside is controlled without increasing a flow rate of the carrier gas. Therefore, detection accuracy for the gas component may be enhanced without increasing supply of the carrier gas, and without providing the entire apparatus in a large size.

In addition, by the correcting of the mass spectrum position, it is possible to correct detection sensitivity differences in analysis devices, day-to-day variations thereof, etc. relative to the mass spectrum position of the gas component. Consequently, it is possible to obtain a precise chromatogram of the gas component.

The area of the chromatogram is influenced by degradation of the ion source ionizing the gas component, measured temperature, etc. Therefore, a sensitivity correction factor is required to be used. The area of the chromatogram about the gas component of the test sample is corrected by using the sensitivity correction factor, thereby precisely quantifying the gas component based on the area of the chromatogram.

In the case of heating the test sample, when the heating rate (temperature rising rate) varies, the shape of chromatogram (time t indicating a maximum peak) also varies, and thus, the area of the chromatogram varies. Therefore, a heating correction factor is required to be used. The heating condition of the heating unit is properly controlled by using the heating correction factor, thereby obtaining a precise chromatogram. Consequently, it is possible to precisely quantify the gas component.

In advance of analyzing a test sample, the corrections using the sensitivity correction factor and the heating correction factor are operated once by using one reference sample, thereby quantifying the measurement target with high accuracy and with a high reproducibility by avoiding detection sensitivity differences in analysis devices as well as day-to-day variations thereof.

When the measurement target includes a plurality of gas components, the method further includes calculating a heating correction factor $H=\Sigma ai \times ti/tsi$ (i: a natural number indicating a gas component i, ai: a well-known heating sensitivity factor of the gas component i, ti: a time indicating a maximum peak of a chromatogram of the gas component i, and tsi: a reference time indicating the maximum peak of the chromatogram of the gas component i).

According to the method for analyzing evolved gas, when the measurement target includes a plurality of gas components, the gas components may be precisely quantified.

The discharged flow rate controlling process may be operated by measuring a predetermined test sample after the correction process.

According to the method for analyzing evolved gas, after the correction process is terminated and the correction is performed, the discharged flow rate controlling process is operated, whereby a detection level of the mass spectrometer is precisely adjusted.

According to another aspect, there is provided an evolved gas analyzer including: a sample holder holding a sample; a heating unit receiving the sample holder therein, and evolving a gas component by heating the sample; an ion source generating ions by ionizing the gas component evolved by the heating unit; a mass spectrometer detecting the gas component by applying mass spectrometry to the ions; a gas channel connecting the heating unit to the mass spectrometer, the gas channel through which mixed gas of the gas component and carrier gas carrying the gas component to the mass spectrometer flows, wherein the gas channel includes a branching channel opened to an outside, and the branching channel includes a discharged flow rate controlling device controlling flow rate of the mixed gas discharged to the outside; a flow rate control device controlling the discharged flow rate controlling device based on a detection signal received from the mass spectrometer so as to control the detection signal to be within a predetermined range; a sample holder supporting unit movably supporting the sample holder so as to move the sample holder to predetermined outer and inner positions of the heating unit; a cooling unit provided at an outside of the heating unit, and cooling the sample holder by being in direct or indirect contact with the sample holder, when the sample holder is moved to a discharging position at which the sample is supplied on or removed from the sample holder; and a correction processing unit using a reference sample including the gas component as a measurement target, wherein the correction processing unit, which is a computer, corrects a mass spectrum position to be located at a reference spectrum position, the mass spectrum position corresponding to a mass-to-charge ratio m/z of a mass spectrum of the gas component of the reference sample; after the correcting of the mass spectrum position, the correction processing unit calculates a sensitivity correction factor Cs=Ss/S by using an area S and a reference area Ss of a chromatogram showing an intensity of the gas component of the reference sample at a retention time, the sensitivity correction factor being used to measure an area of a chromatogram of the gas component of a test sample; and calculates a heating correction factor H=t/ts by using a time t and a reference time is indicating a maximum peak of the chromatogram of the gas component of the reference sample, the heating correction factor being used to correct a heating rate of the test sample in the heating unit, when measuring the gas component of the test sample.

According to the method for analyzing evolved gas and the evolved gas analyzer, it is possible to correct detection sensitivity differences in analysis devices, day-to-day variations thereof, etc., thereby quantifying the measurement target with high accuracy. In addition, it is possible to perform a proper correction or adjustment of the evolved gas analyzer depending on the measurement target without professional knowledge or experience.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
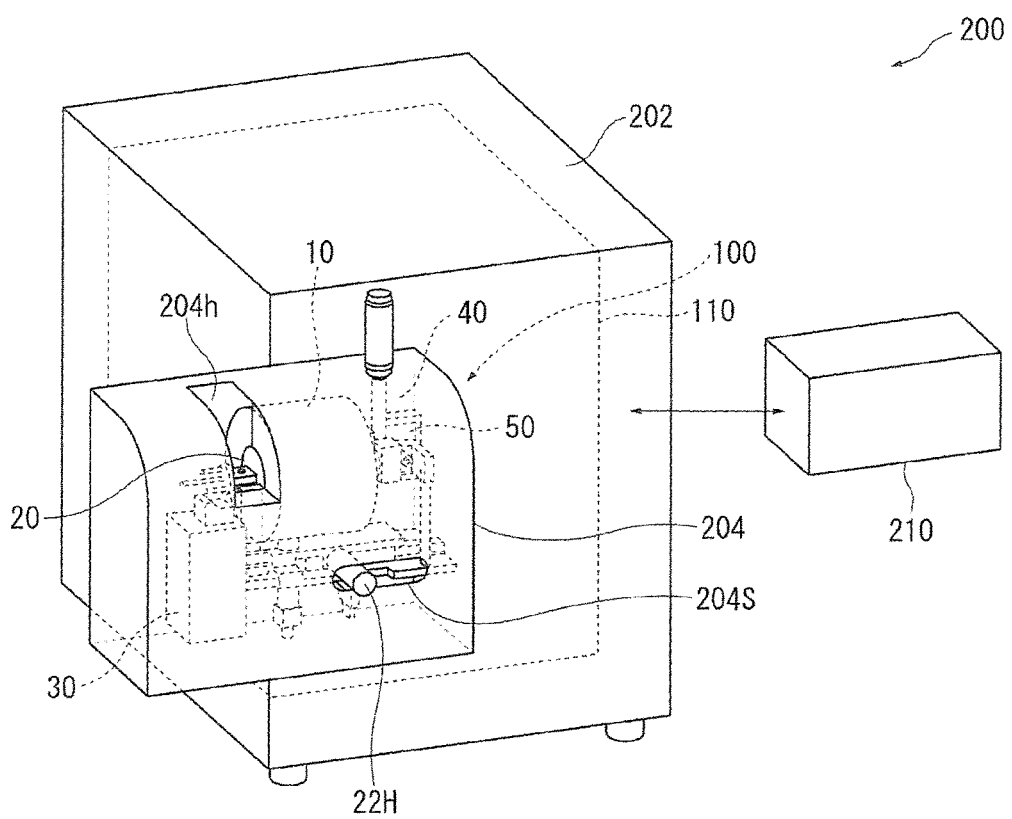
FIG. 1 is a perspective view showing the configuration of an evolved gas analyzer according to an exemplary embodiment of the present invention.
Figure 2:
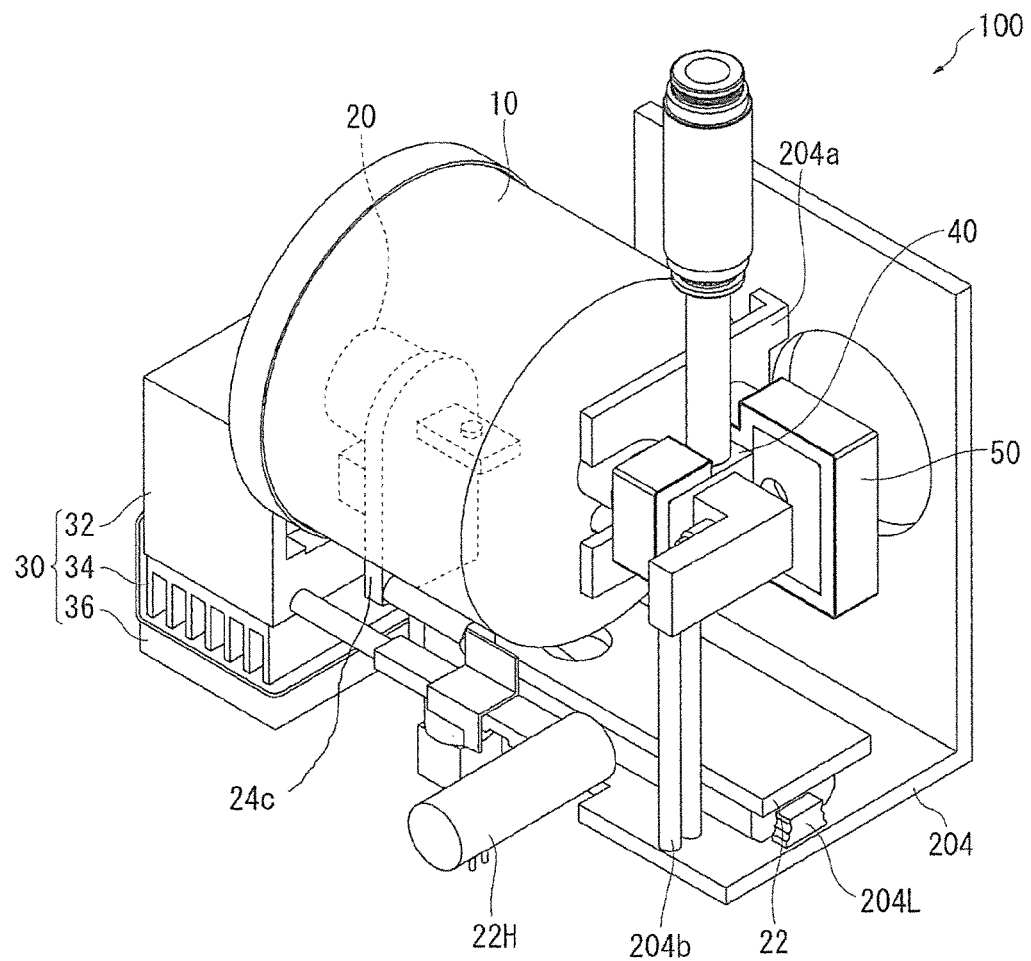
FIG. 2 is a perspective view showing the configuration of a gas evolving unit.
Figure 3:
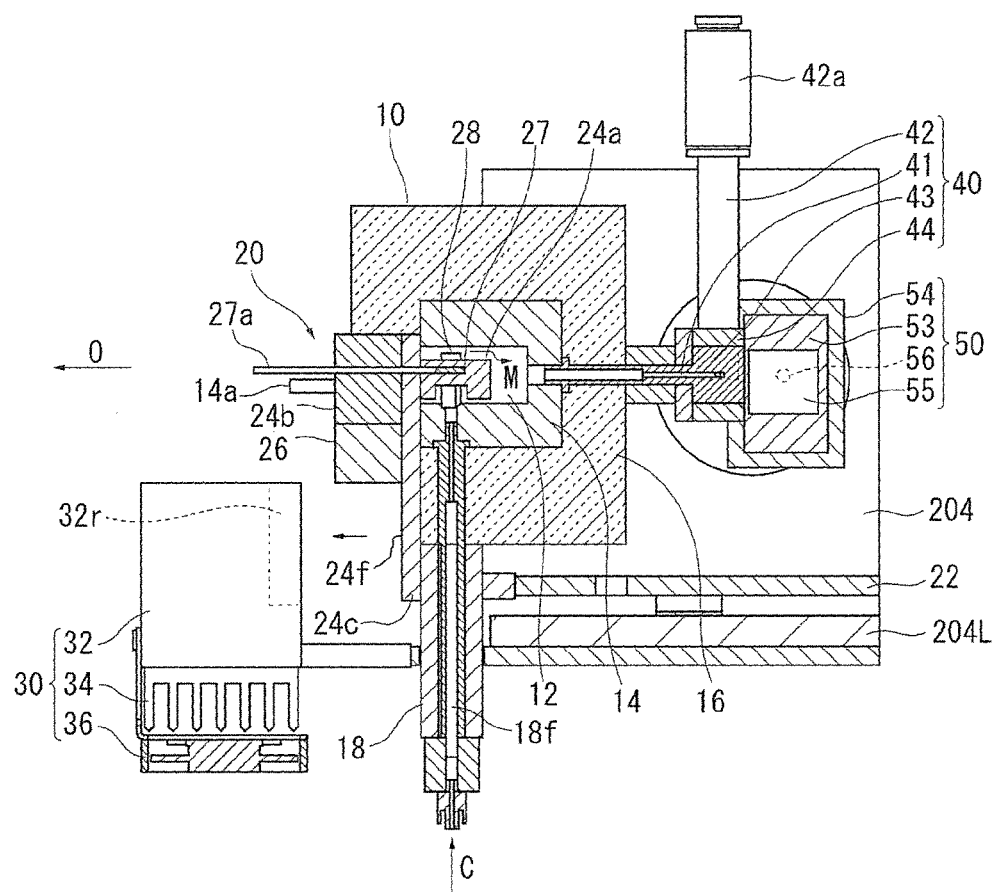
FIG. 3 is a longitudinal sectional view showing the configuration of the gas evolving unit.
Figure 4:
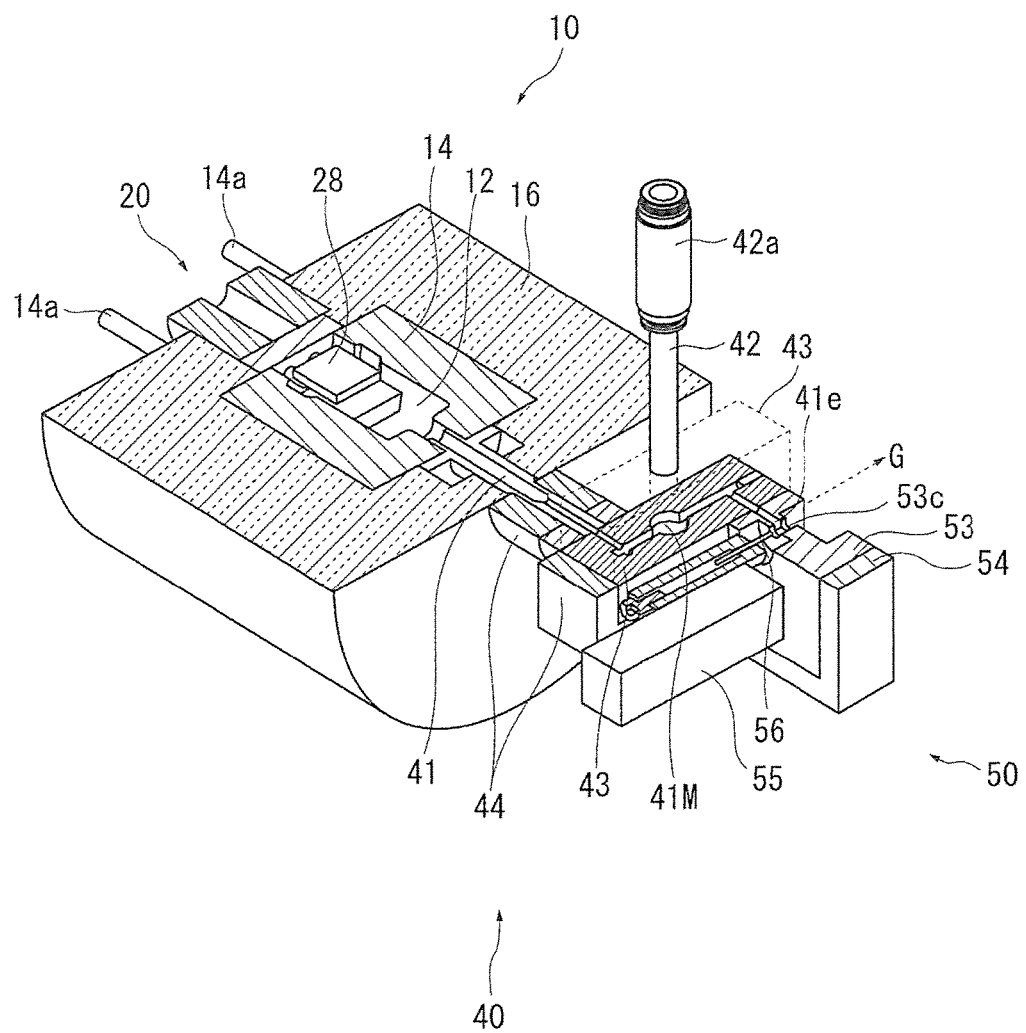
FIG. 4 is a cross-sectional view showing the configuration of the gas evolving unit.

Hereinafter, the exemplary embodiment of the present invention will be described with reference to the accompanying drawings. FIG. 1 is a perspective view showing the configuration of an evolved gas analyzer 200. FIG. 2 is a perspective view showing the configuration of a gas evolving unit 100. FIG. 3 is a longitudinal sectional view showing the configuration of the gas evolving unit 100 on an axis O. FIG. 4 is a cross-sectional view showing the configuration of the gas evolving unit 100 on the axis O.

The evolved gas analyzer 200 includes a body unit 202 that is a housing; an attaching unit 204 for a gas evolving unit, the attaching unit having a box shape and attached at a front surface of the body unit 202; and a computer (control device) 210 controlling the evolved gas analyzer. The computer 210 includes a CPU processing data, a memory unit storing a computer program and data, an input unit such as a monitor, a keyboard, etc. The computer 210 is a correction processing unit in the appended claims.

In the attaching unit 204 for the gas evolving unit, there are a heating furnace (heating unit) 10 having a cylinder shape; a sample holder 20; a cooling unit 30; a splitter 40 splitting gas; and the gas evolving unit 100 having an ion source 50. In addition, a mass spectrometer (detecting device) 110 is provided in the body unit 202. The mass spectrometer analyzes gas components evolved by heating a sample.

In addition, an opening 204h is provided at an upper surface of the attaching unit 204 for the gas evolving unit, while being provided at a front surface thereof. The sample holder 20 is located at the opening 204h by being moved toward a discharging position that is located at an outside of the heating furnace 10. Therefore, a sample may be supplied on or removed from the sample holder 20 through the opening 204h. In addition, a slit 204s is provided at the front surface of the attaching unit 204. By moving an opening/closing handle 22H exposed to an outside of the attaching unit through the slit, the sample holder 20 is moved into or from the heating furnace 10. Therefore, the sample holder is set at the discharging position, and thus, the sample is supplied on or removed from the sample holder.

In addition, for example, when the sample holder 20 is moved on a movement rail 204L (after mentioned) by a stepping motor, etc. controlled by the computer 210, the sample holder 20 may be automatically moved into or from the heating furnace 10.

Hereinafter, the configuration of the gas evolving unit 100 will be described with reference to FIGS. 2 to 5.

First, the heating furnace 10 is attached to an attaching plate 204a of the attaching unit 204 by being parallel to the axis O. The heating furnace includes a heating chamber 12 having a cylinder shape and being opened on the axis O; a heating block 14; and a heat retaining jacket 16.

The heating block 14 surrounds the heating chamber 12, and the heat retaining jacket 16 surrounds the heating block 14. The heating block 14 is made of aluminum, and is heated by electricity from a pair of heating unit heaters 14a extending from the heating furnace 10 to outside in a direction of the axis O as shown in FIG. 4. The heating unit heaters 14a heat (retains the heat of) the heating block 14, and air in the heating chamber 12 surrounded by the heating block 14 to a predetermined temperature.

In addition, the attaching plate 204a extends in a direction perpendicular to the axis O. The splitter 40 and the ion source 50 are attached to the heating furnace 10. In addition, a supporter 204b extends in a vertical direction of the attaching unit 204, and supports a staying unit 55 of the ion source 50.

The splitter 40 is connected to an opposite side (right side of FIG. 3) of an opening side of the heating furnace 10. In addition, a carrier gas protecting pipe 18 is connected to a lower side of the heating furnace 10. The carrier gas protecting pipe 18 surrounds a carrier gas channel 18*f* connected to a lower surface of the heating chamber 12. Carrier gas C is introduced into the heating chamber 12 through the carrier gas channel.

In addition as described in detail after, a gas channel 41 communicates with a cross section on the opposite side (right side of FIG. 3) of an opening side of the heating chamber 12. Mixed gas M of the carrier gas C and a gas component G evolved by the heating furnace 10 (heating chamber 12) flows through the gas channel 41.

The sample holder 20 includes a stage 22 moving on the movement rail 204L attached to an inner upper surface of the attaching unit 204; a bracket 24*c* attached on the stage 22 and extending in a vertical direction; insulators 24*b* and 26 attached to a front surface (left side of FIG. 3) of the bracket 24*c*; a sample holding unit 24*a* extending from the bracket 24*c* in a direction of the axis O in the heating chamber 12; a sample heater 27 provided just below the sample holding unit 24*a*; and a sample plate 28 provided on an upper surface of the sample holding unit 24*a* above the sample heater 27, the sample plate on which the sample is placed.

Here, the movement rail 204L extends in a direction of the axis O (horizontal direction of FIG. 3), and the stage 22 of the sample holder 20 moves in the direction of the axis O. In addition, the opening/closing handle 22H extends in a direction perpendicular to the axis O, and is attached to the stage 22.

The movement rail 204L is a sample holder supporting unit in the appended claims.

In addition, an upper portion of the bracket 24*c* has a semicircular shape and a lower portion of the bracket has a rectangular shape. Referring to FIG. 2, the insulator 24*b* has a substantially cylinder shape, and is provided at a front surface of an upper portion of the bracket 24*c*. An electrode 27*a* of the sample heater 27 penetrates the insulator 24*b*, and protrudes to an outside of the gas evolving unit. The insulator 26 has a rectangular shape, and is provided at the front surface of the bracket 24*c*. The insulator 26 is located lower than the insulator 24*b*. In addition, the insulator 26 is not provided at a lower portion of the bracket 24*c*, and a front surface of the lower portion of the bracket 24*c* is exposed to form a contact surface 24*f*.

The bracket 24*c* has a diameter slightly larger than a diameter of the heating chamber 12 such that the bracket 24*c* seals the heating chamber 12. The sample holding unit 24*a* is located in the heating chamber 12.

In addition, the sample placed on the sample plate 28 in the heating chamber 12 is heated in the heating furnace 10 such that the gas component G is evolved.

The cooling unit 30 faces the bracket 24*c* of the sample holder 20, and is located outside of the heating furnace 10 (left side of the heating furnace 10 in FIG. 3). The cooling unit 30 includes a cooling block 32 having a concave portion 32*r* that has a rectangular shape; cooling fins 34 connected to a lower surface of the cooling block 32; and an air cooling fan 36 connected to a lower surface of the cooling fins 34, and blowing air to the cooling fins 34.

In addition as described in detail after, when the sample holder 20 moves in a direction of the axis O on the movement rail 204L toward a left side of FIG. 3, and comes out of the heating furnace 10, the contact surface 24*f* of the bracket 24*c* is positioned at the concave portion 32*r* of the cooling block 32 by being in contact with the concave portion. Consequently, as heat of the bracket 24*c* is removed by the cooling block 32, the sample holder 20 (particularly, the sample holding unit 24*a*) is cooled.

In addition, according to the exemplary embodiment of the present invention, the sample holder 20 (including the bracket 24*c*) and the cooling block 32 are made of aluminum.

As shown in FIGS. 3 and 4, the splitter 40 includes the gas channel 41 connected to the heating chamber 12; a branching channel 42 connected to the gas channel 41, and opened to the outside; a mass flow controller (discharged flow rate controlling device) 42*a* connected to a discharge side of the branching channel 42 to control flow rate of the mixed gas M discharged from the branching channel 42 to the outside; a housing unit 43 opening the gas channel 41 therein; and a heat retaining unit 44 surrounding the housing unit 43.

As shown in FIG. 4, when viewed from the top, the gas channel 41 is connected to the heating chamber 12 and extends in a direction of the axis O and next, bends in a direction perpendicular to the axis O, and bends again in a direction of the axis O such that the gas channel reaches an end part 41*e*. The gas channel has a crank shape. In addition, a portion of the gas channel 41 that extends in a direction perpendicular to the axis O is provided with a center thereof having a circular shape that has a diameter larger that a diameter of the gas channel to define a branch chamber 41M. The branch chamber 41M extends to an upper surface of the housing unit 43. The branch chamber 41M is fitted with the branching channel 42 having a diameter slightly smaller than that of the branch chamber 41M.

The gas channel 41 may have a straight line shape extending in a direction of axis O from the heating chamber 12 connected with the gas channel to the end part 41*e*. Alternatively, depending on a positional relationship with the heating chamber 12 or with the ion source 50, the gas channel 41 may have a variously curved shape, a line shape having an angle to the axis O, etc.

In addition, according to the exemplary embodiment of the present invention, the gas channel 41 has a diameter about 2 mm, and the branch chamber 41M and the branching channel 42 have respective diameters about 1.5 mm. In addition, a ratio (split ratio) of flow rates from the gas channel 41 to the end part 41*e*, and flow rates branched to the branching channel 42 is determined by flow resistance. The mixed gas M may flow more through the branching channel 42. In addition, the split ratio is controlled by adjusting an opening ratio of the mass flow controller 42*a*.

As shown in FIGS. 3 and 4, the ion source 50 includes an ionizer housing unit 53; an ionizer heat retaining unit 54 surrounding the ionizer housing unit 53; a discharge needle 56; and a staying unit 55 fixing the discharge needle 56. The ionizer housing unit 53 has a plate shape, and a surface of the plate is parallel to the axis O. A small hole 53C penetrates the center of the surface of the plate. In addition, the end part 41*e* of the gas channel 41 passes through the ionizer housing unit 53, and faces a side wall of the small hole 53C. In the meantime, the discharge needle 56 extends in a direction perpendicular to the axis O, and faces the small hole 53C.

In addition, in the mixed gas M introduced around the small hole 53C from the end part 41*e*, the gas component G is ionized by the discharge needle 56.

The ion source 50 is a well-known device. According to the exemplary embodiment of the present invention, atmospheric pressure chemical ionization (APCI) is applied to the ion source. APCI causes minimal fragmentation of the gas component G, such that fragmentation peak does not occur.

Therefore, it is possible to detect the measurement target without separating the gas component G by using a chromatograph, etc.

The gas component G ionized at the ion source 50 and the carrier gas C are introduced to the mass spectrometer 110, and are analyzed.

In addition, the ion source 50 is contained in the ionizer heat retaining unit 54.

Figure 5:
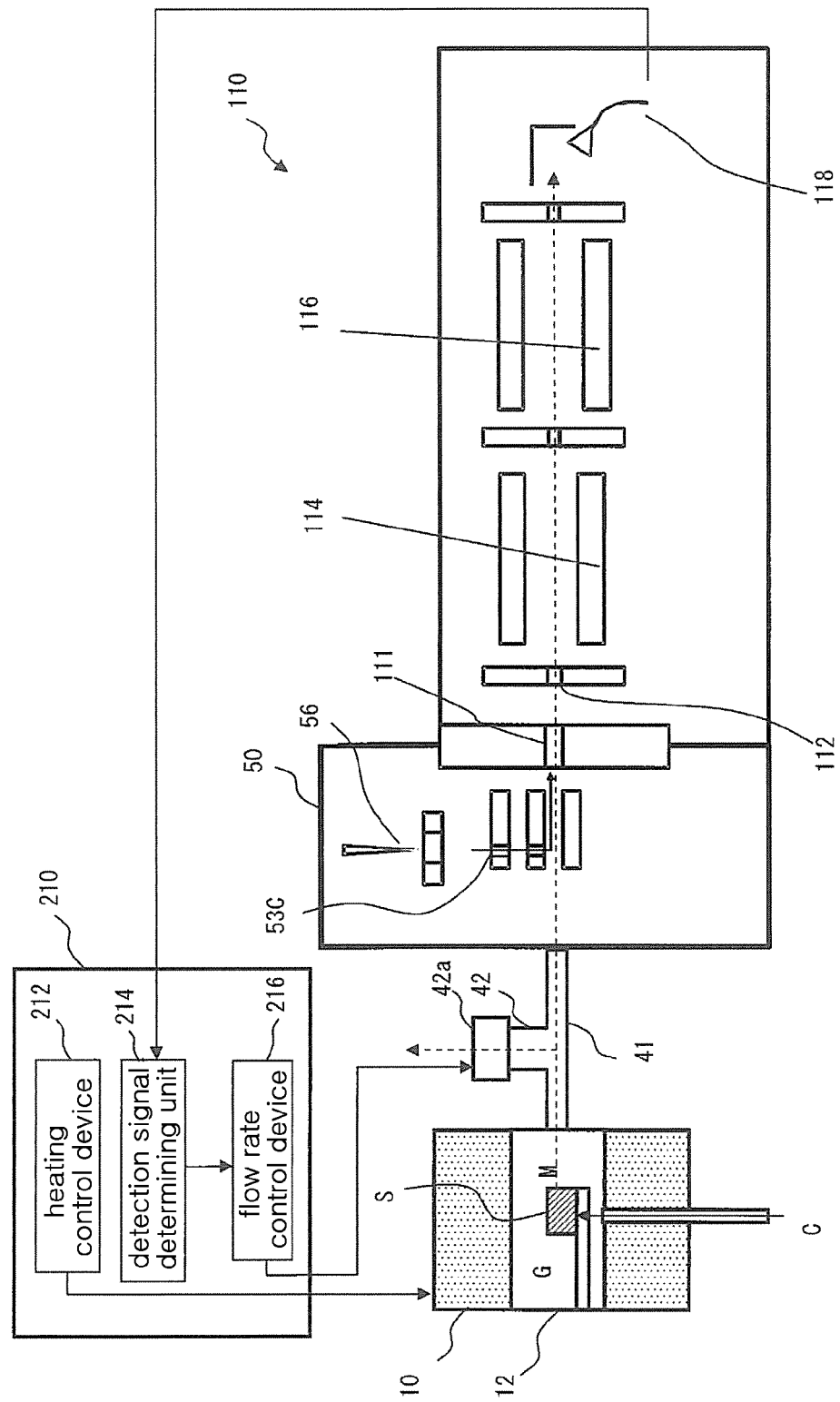
FIG. 5 is a block diagram showing a process of analyzing a gas component by the evolved gas analyzer.

FIG. 5 is a block diagram showing a process of analyzing a gas component by the evolved gas analyzer 200.

The sample S is heated in the heating chamber 12 of the heating furnace 10, and the gas component G is evolved. Heating condition (temperature rising rate, maximum temperature, etc.) of the heating furnace 10 is controlled by a heating control device 212 of the computer 210.

The gas component G is mixed with the carrier gas C introduced in the heating chamber 12 to be a mixed gas M, and the mixed gas M is introduced in the splitter 40. A detection signal determining unit 214 of the computer 210 receives a detection signal from a detector 118 of the mass spectrometer 110.

A flow rate control device 216 determines whether or not peak intensity of the detection signal received from the detection signal determining unit 214 is within a threshold range. When the peak intensity is out of the threshold range, the flow rate control device 216 controls the opening ratio of the mass flow controller 42*a*. Therefore, a flow rate of the mixed gas M discharged from the splitter 40 to an outside through the branching channel 42 is controlled, and further, a flow rate of the mixed gas M introduced from the gas channel 41 into the ion source 50 is controlled, thereby optimizing a detection accuracy of the mass spectrometer 110.

The mass spectrometer 110 includes a first fine hole 111 through which the gas component G ionized at the ion source 50 is introduced; a second fine hole 112 through which the gas component G flows, after the first fine hole 111; an ion guide 114; a quadrupole mass filter 116; and the detector 118 detecting the gas component G discharged from the quadrupole mass filter 116.

The quadrupole mass filter 116 varies an applied high frequency voltage such that mass is scanned. The quadrupole mass filter generates a quadrupole electric field, and detects ions by moving the ions like a pendulum swinging within the quadrupole electric field. The quadrupole mass filter 116 functions as a mass separator passing only gas component G within a certain mass range such that the detector 118 may identify and quantify the gas component G.

In addition, in comparison with an entire ions detection (scan) mode detecting ions of a certain range of a mass-to-charge ratio, when using a selected ion detection (SIM) mode detecting only ions of a certain mass-to-charge ratio m/z of a gas component, which is a measurement target, a detection accuracy of the gas component, which is the measurement target, increases.

Figure 6A:
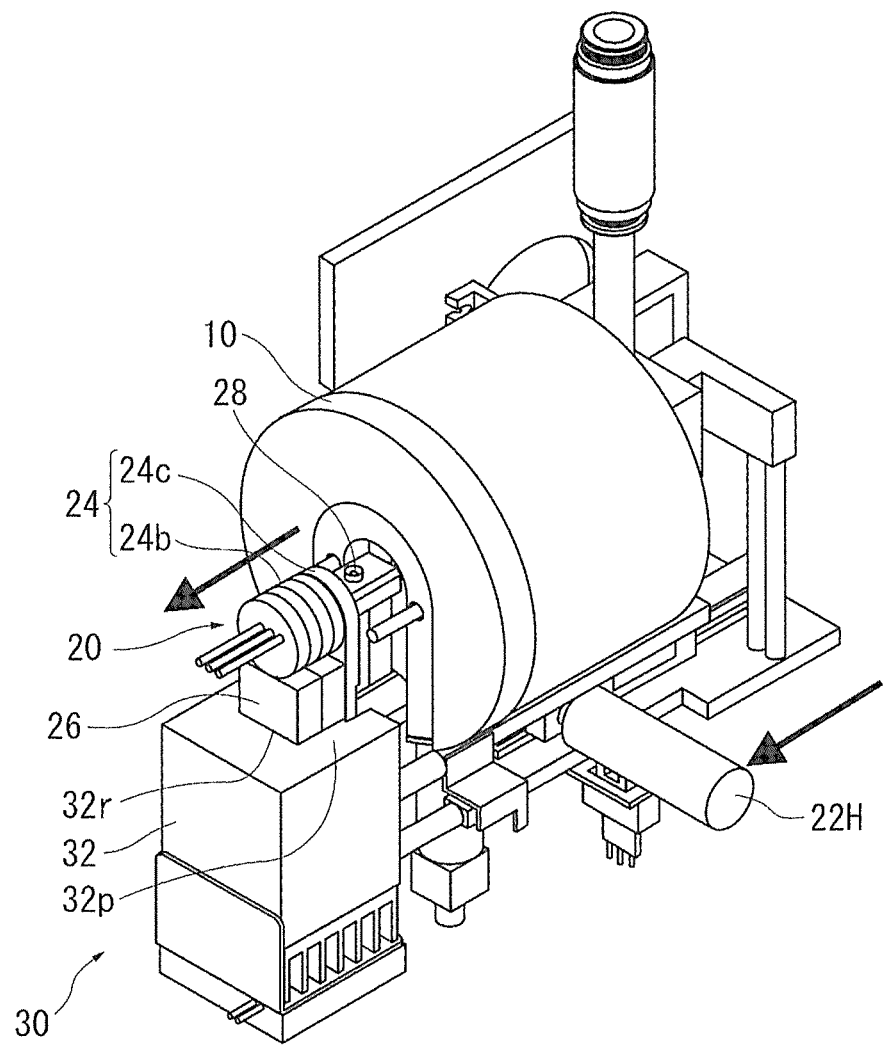
FIGS. 6A and 6B are views respectively showing a discharging position and a measuring position of the sample holder.
Figure 6B:
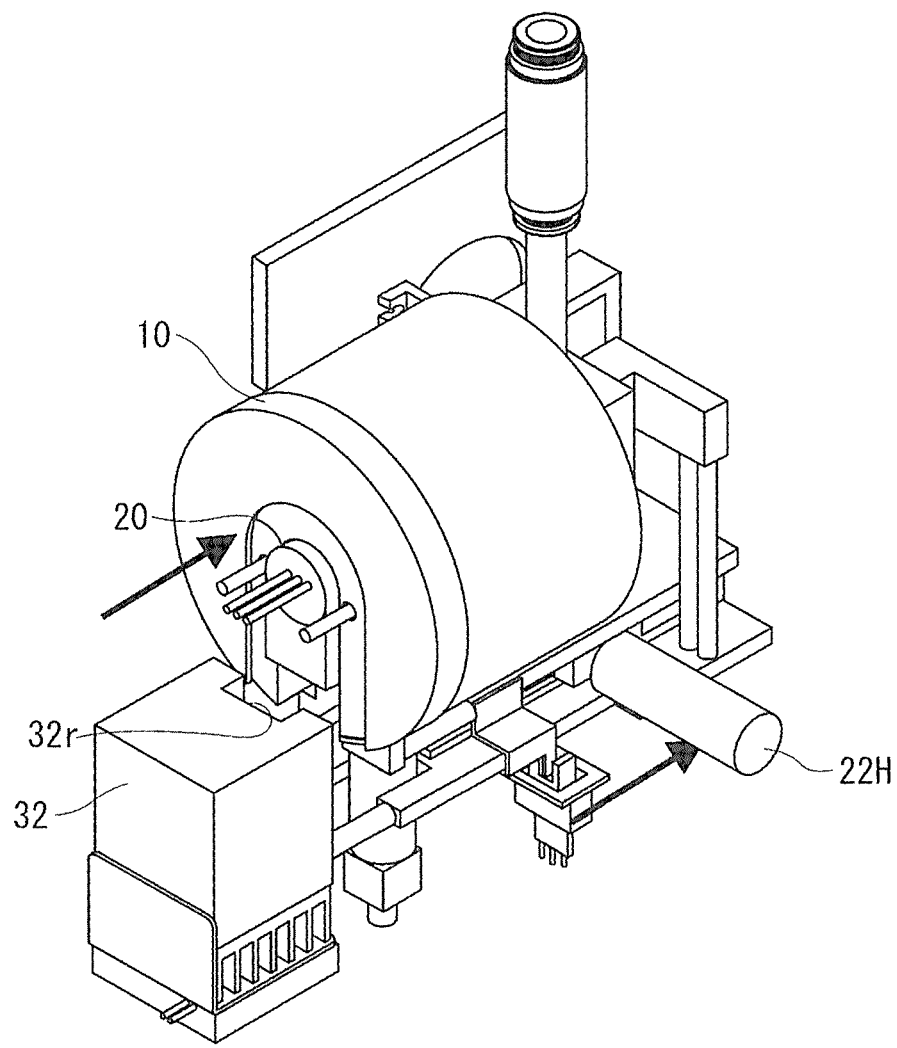

Hereinafter, cooling of the sample holder 20 will be described with reference to FIGS. 6A and 6B. According to the exemplary embodiment of the present invention, the sample holder 20 moves in the direction of axis O intervened by the stage 22 between predetermined two positions (a discharging position at which the sample plate 28 is discharged and located at an outside of the heating furnace 10 as shown in FIG. 6A, and a measuring position at which the gas component is measured and the sample plate 28 is located in the heating furnace 10 as shown in FIG. 6B). gas component First, at the discharging position shown in FIG. 6A, when the sample plate 28 and the sample are supplied on or removed from the sample holder, the sample plate 28 and the sample are replaced, and are heated from about a room temperature to start the next analysis. Here, in case when the sample holder 20 is too hot, when the sample plate 28 is located in the sample holder, the sample begins to be heated in advance of the analysis. Therefore, in order to prevent this, the sample holder 20 is naturally cooled, but standby time to cool the sample holder 20 is too long.

Therefore, as shown in FIG. 6A, when the sample holder 20 is moved to the discharging position, the contact surface 24*f* of the bracket 24*c* is in contact with the concave portion (contact portion) 32*r* of the cooling block 32. Therefore, heat of the bracket 24*c* is cooled by the cooling block 32, and thus the sample holder 20 is cooled.

In comparison with the natural cooling, the sample holder 20 is rapidly cooled, and thus it is possible to enhance the analysis work efficiency. In addition, the sample holder 20 is cooled at an outside of the heating furnace 10 such that the cooling unit 30 is not exposed to high temperature air of the heating furnace 10. Therefore, excessive cooling performance is unnecessary, and the cooling unit 30 or the entire apparatus is provided in a small size. In addition, the temperature of the heating block 14 is not reduced by the cooling, such that it is unnecessary to use extra energy and time to heat the heating furnace 10 again.

In addition, it is unnecessary to provide the cooling unit 30 in the heating furnace 10, whereby the heating furnace 10 or the entire apparatus may be provided in a small size.

Figure 7:
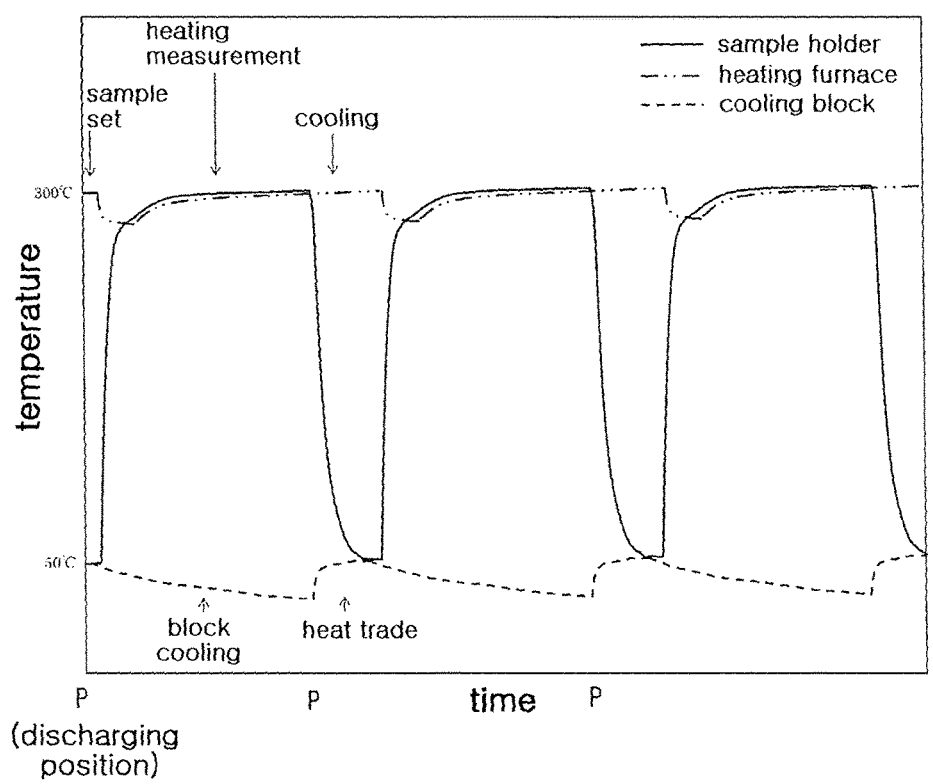
FIG. 7 is a view showing an example of a heating pattern of a heating unit, and of temperature changes of both a sample holder and a cooling unit.

FIG. 7 is a view showing an example of a heating pattern of the heating furnace 10 controlled by the heating control device 212, and of temperature changes of both the sample holder 20 and the cooling block 32. Here, retention temperature (maximum temperature) of the heating furnace 10 is 300° C., and heating start temperature of the sample is under 50° C.

First, at time 0 (when the sample holder 20 is moved to the discharging position of FIG. 6A), the sample is placed on the sample plate 28 of the sample holder 20 having 50° C. Here, the cooling block 32 has been already cooled to a room temperature, and the cooling block is heated up to about 50° C. by being in contact with the sample holder 20. In the meantime, the sample holder 20 is heated to about 50° C. In addition, air temperature in the heating furnace 10 is controlled by the heating unit heater 14*a* to be 300° C.

Next, the sample holder 20 cooled to about 50° C. is moved to the measuring position of FIG. 6B. When the sample holder is moved into the heating chamber 12, the heating furnace 10 controlled to be 300° C. and the sample heater 27 provided in just below the sample holding unit 24*a* cause the sample holder 20 to be heated to 300° C., and an evolved gas component is analyzed. During the analyzing, the cooling block 32 is cooled to under 50° C. (about room temperature) by the air cooling fan 36, etc.

After the analysis, the sample holder 20 is moved to the discharging position P again, and the above-described heating cycle is repeated.

Here, the cooling unit 30 is provided at an outside of the heating furnace 10, and the cooling unit 30 heated by cooling the sample holder 20 is slowly cooled during the analysis. Particularly, as shown in FIG. 7, generally, time for the analysis is longer than time for cooling. Therefore, it is unnecessary to rapidly cool the cooling unit 30 by using water cooling, etc. It is sufficient to apply natural cooling by the cooling fins 34, or apply forced air cooling by the air cooling fan 36. In comparison with the water cooling, etc., the structure of the cooling unit 30 is simple, whereby the entire apparatus may have reduced costs or may be provided in a small size.

In addition, as shown in FIG. 6A, when viewed from the top of the cooling block 32, a pair of protruding portions 32*p* having a U shape protrudes from respective opposite ends of the concave portion (contact portion) 32*r* toward the heating furnace 10 so as to surround the sample holder 20 by the protruding portions 32*p*. Therefore, the sample holder 20 is moved to the concave portion 32*r* to be sufficiently located at an outside of the heating furnace 10. In addition, capacity (heat capacity) of the cooling block 32 increases by comparison with a cooling block having no protruding portions 32*p*, thereby enhancing cooling performance.

In addition, in order to maintain the same capacity of the cooling block 32 without the protruding portions 32*p*, it is required to move the cooling block 32 more toward an outside (left side of FIG. 6A) of the heating unit 10, whereby it results in a large size of the entire apparatus. Therefore, it is possible to provide the entire apparatus in a small size by providing the protruding portions 32*p*.

In addition, when a ratio C1/C2 of a heat capacity C1 of the cooling block 32 to a heat capacity C2 of the sample holder 20 is within a range of 5 to 20, it is possible to provide the entire apparatus in a small size and to enhance cooling performance. When the ratio is less than 5, the heat capacity C1 of the cooling block 32 is reduced, and thus the cooling performance may also be reduced. If the cooling performance is insufficient, the cooling block may not be sufficiently cooled to the heating start temperature. When the ratio exceeds 20, the size of the cooling block 32 is too large, whereby it results in a large size of the entire apparatus.

In addition, it is desired that the cooling unit 30 is provided with the air cooling fan 36 or with the cooling fins 34 cooling the cooling block 32. Therefore, the structure of the cooling unit 30 is simple, and thus, the entire apparatus may have reduced costs or may be provided in a small size, in comparison with the case when water cooling is applied to the cooling unit 30 or with the case when a duct, which refrigerant gas flows through, is attached to the cooling unit 30.

In case of a heat sink provided with the cooling fins 34 attached to the cooling block 32, the cooling fins 34 naturally cool the cooling block 32.

However, when the cooling block 32 is insufficiently cooled, it is desired that the air cooling fan 36 is also attached thereto so as to apply forced air cooling to the cooling block 32. In addition, according to the exemplary embodiment of the present invention, as shown in FIGS. 2, 6A and 6B, the cooling fins 34 are connected to the lower surface of the cooling block 32, and the air cooling fan 36 is connected to the lower surface of the cooling fins 34.

In addition, according to the exemplary embodiment of the present invention, the heating furnace 10 includes both the heating unit heater 14*a* heating an inside of the heating furnace (heating chamber 12) to a predetermined temperature, and the sample heater 27 heating the sample in the sample holder 20.

Therefore, the heating unit heater 14*a* heats (retains the heat of) air in the heating furnace (heating chamber 12) to the predetermined temperature such that it is possible to prevent the temperature of the sample in the heating chamber 12 from being changed. In addition, the sample heater 27 provided around the sample may locally heat the sample, and thus, the temperature of the sample rapidly increases.

In addition, in terms of rapidly increasing the temperature of the sample, it is desired that the sample heater 27 is positioned around a unit on which the sample is placed (for example, the sample plate 28). Particularly, it is desired that the sample heater 27 is provided under the sample plate 28 in the sample holder 20.

According to the exemplary embodiment of the present invention, as shown in FIGS. 3 and 4, the gas channel 41 includes a branching channel 42 opened to the outside. An opening ratio of a mass flow controller 42*a* attached to the branching channel 42 is controlled to adjust flow rate of the mixed gas M discharged from the branching channel 42 to the outside, and to adjust flow rate of the mixed gas M introduced from the gas channel 41 into the ion source 50.

Therefore, when a plurality of gas components are evolved and thus, gas density is too high. The flow rate of the mixed gas M discharged from the branching channel 42 to the outside is increased, and the flow rate of the mixed gas M introduced from the gas channel 41 into the ion source 50 is decreased. Therefore, it is possible to avoid that the gas density exceeds the detection range of the mass spectrometer 110 and thus, the detection signal is overly scaled, whereby the measurement is inaccurate.

Here, the flow rate of the mixed gas discharged from the branching channel 42 to the outside is controlled without increasing flow rate of the carrier gas. Therefore, detection accuracy for the gas component may be enhanced without increasing supply of the carrier gas, and without providing the entire apparatus in a large size.

In addition, when using the mass spectrometer as the detecting device, the gas component is ionized at the front thereof, which is the ion source 50. However, when the plurality of gas components are evolved, accessory substances are ionized. Thus, the ion-suppression occurs, and the detection signal is degraded.

Therefore, in case of the ion-suppression, the flow rate control device 216 determines the peak intensity of the detection signal of the mass spectrometer 110 received from the detection signal determining unit 214 is less than a threshold value. Next, the flow rate control device 216 transmits a control signal to the mass flow controller 42*a* to increase the opening ratio. Therefore, the flow rate of the mixed gas M introduced into the ion source 50 is reduced, and the ionization of the accessory substances and the degradation of the detection signal are prevented, whereby the detection accuracy for the gas component may be enhanced.

In addition, it is difficult to determine whether or not the ion-suppression occurs by only obtaining the peak intensity of the detection signal. Also, the measurement target may have low content of the gas component. Therefore, it is required to determine whether or not the ion-suppression occurs due to high content of concomitant, etc. that is not the measurement target. The determination is performed by a user or the flow rate control device 216 based on a table storing that whether or not the ion-suppression occurs at each sample or at each gas component.

In addition, the flow rate control device 216 generates a control signal to increase the flow rate of the mixed gas M discharged from the branching channel 42 to the outside, when the peak intensity of the detection signal exceeds the threshold value (overly scaled) or less than the threshold value (when determining the ion-suppression occurs).

In this case, for example, the table stores that whether or not the ion-suppression occurs at each gas component, and the flow rate control device 216 determines the ion-suppression based on the table. When determining the ion-suppression occurs, a control signal for increasing the opening ratio is transmitted to the mass flow controller 42*a*. In addition, when measured by the user, whether or not the measurement indicates the ion-suppression is inputted by an input unit (select button, etc.) of the computer 210. The flow rate control device 216 compares the peak intensity of the detection signal with the threshold value based on the input signal, and transmits a control signal for increasing the opening ratio to the mass flow controller 42a.

In addition, when the measurement target is phtalates and the accessory substance is additive agent of phthalate etc. as an example, the ion-suppression occurs.

In addition, the gas component evolved in the heating furnace 10 may be cooled, condensed, and trapped at the gas channel 41 located close to the branch chamber 41M and at an inner wall of the branching channel 42, and next, may be vaporized and measured in the ion source 50. In this case, measurement is performed for a long time and thus, work efficiency is degraded. In addition, the gas component which is condensed and vaporized may influence the next measurement.

Figure 8:
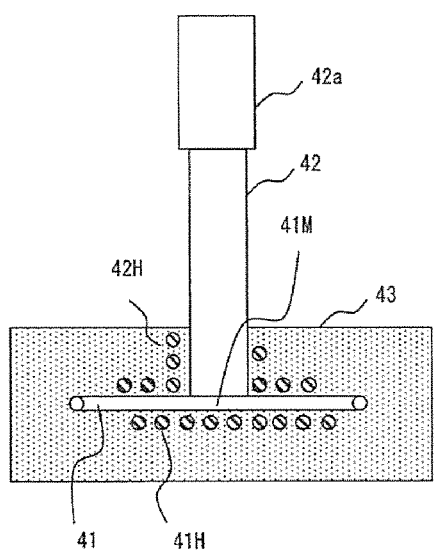
FIG. 8 is a view showing a gas channel and heat retaining parts of a branching channel.

Therefore, as shown in FIG. 8, heat retaining parts 41H and 42H may be provided to heat or retain the heat of the perimeter of at least one of the gas channel 41 located close to the branch chamber 41M and the branching channel 42. Therefore, it is possible to prevent the gas component being trapped at the gas channel 41 or at the inner wall of the branching channel 42.

In addition, referring to FIG. 8, the heat retaining part 41H is a coil heater heating the perimeter of the gas channel 41 located close to the branch chamber 41M, and the heat retaining part 42H is a coil heater heating the perimeter of the branching channel 42 located close to the branch chamber 41M.

In addition, the heat retaining parts 41H and 42H are not limited to heaters, and may be an insulator, etc. that can prevent coagulation of the gas component. In addition, it is possible to provide at least one of the heat retaining parts 41H and 42H, or both.

In the meantime, when the gas component (mixed gas) is heated by the heat retaining parts 41H and 42H, the mixed gas discharged from the branching channel 42 and flowing through the mass flow controller 42a starts to have high temperature. Therefore, a heating resisting type mass flow controller 42a may be required.

Figure 9:
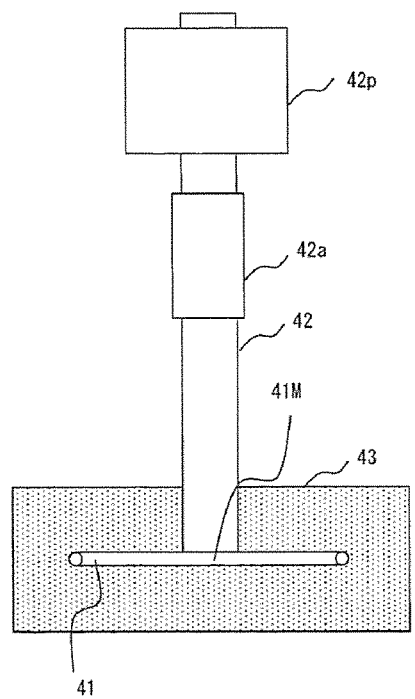
FIG. 9 is a view showing a forced discharge unit of the branching channel.

As shown in FIG. 9, without the heat retaining parts 41H and 42H, a discharge pump (forced discharge unit) 42p may be provided at the branching channel 42, which is closer to the outgoing side than the mass flow controller (42a). Therefore, the mixed gas M flowing through the branching channel 42 is forced to be discharged, and air pressure of the gas channel 41 located close to the branch chamber 41M and of the branching channel 42 is reduced, whereby the trapped gas component is prevented to flow backward to the ion source 50.

Hereinafter, a method for analyzing evolved gas according to the exemplary embodiment of the present invention will be described with reference to FIG. 10.

A reference sample including a gas component as a measurement target is prepared. According to the exemplary embodiment of the present invention, the measurement target includes a plurality of gas components, and the reference sample includes the plurality of gas components (for example, diethylhexyl phthalate (DEHP), dibutyl phthalate (DBP), benzylbutyl phthalate (BBP), and diisobutyl phthalate (DIBP), that are four substances of the phtalates restricted under RoHS). Gas component contents of the reference sample are not limited. However, it is better to respectively set the gas component contents of the reference sample close to assumed gas component contents of a test sample (for example, it is desirable to set four gas component contents to the same digit numbers because RoHS limits DEHP, DBP, BBP, and DIBP at 1000 ppm). In addition, a gas component content of a sample is (mass of a gas component)/(entire mass of a sample).

Next, a correction is performed in sequence as follows.

(1) First, a mass spectrum position is corrected to be located at a reference spectrum position, the mass spectrum position corresponding to a mass-to-charge ratio m/z of a mass spectrum of each gas component of the reference sample. For example, referring to FIG. 10, in order to respectively locate mass spectrum positions of three gas components 1, 2, and 3 within allowable ranges 2L of reference spectrum positions m1, m2, and m3, settings (for example, high frequency voltage) of the mass spectrometer (quadrupole mass filter 116) 110 are adjusted.

Figure 11:
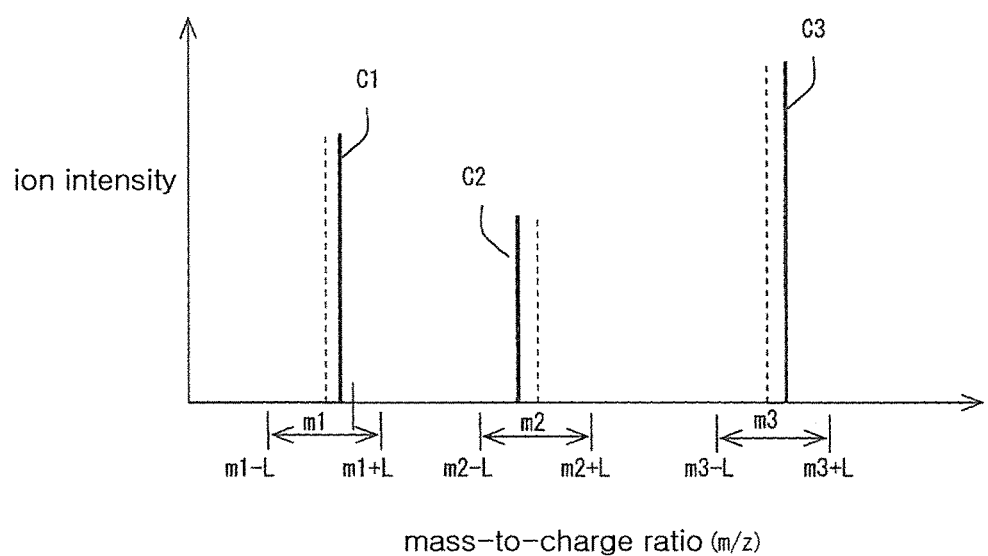
FIG. 11 is a view showing a method for correcting the evolved gas analyzer according to the exemplary embodiment of the present invention.

In addition, as shown in FIG. 11, an allowable range 2L is a range within ±L of each of reference spectrum positions m1, m2, and m3. It is desired that the mass spectrum positions of gas components of the reference sample are located within respective allowable ranges 2L. According to the exemplary embodiment of the present invention, the gas components in the reference sample are predetermined. Therefore, unlike a general-purpose analysis using undefined measurement targets, it is not necessary to perform an adjustment minimizing differences between the mass spectrum positions and the reference spectrum positions of gas components. However, a method of correcting the mass spectrum positions to be located at respective reference spectrum positions is not limited thereto, and the adjustment may be performed.

As described above, it is possible to correct detection sensitivity differences in analysis devices, day-to-day variations thereof, etc. relative to the mass spectrum positions of the gas components, thereby precisely obtaining chromatograms of the gas components that will be described hereinafter.

(2) Second, after the correcting of the mass spectrum position in (1), a sensitivity correction factor $Cs=Ss/S$ is calculated by using an area S and a reference area Ss of a chromatogram showing an intensity (ion intensity) of the gas component of the reference sample at a retention time gas component. Cs is a correction factor when measuring an area of a chromatogram of the gas component of the test sample. The area S of the chromatogram is influenced by degradation of the ion source ionizing the gas components, measured temperature, etc. Therefore, the sensitivity correction factor is required to be used.

Figure 10:
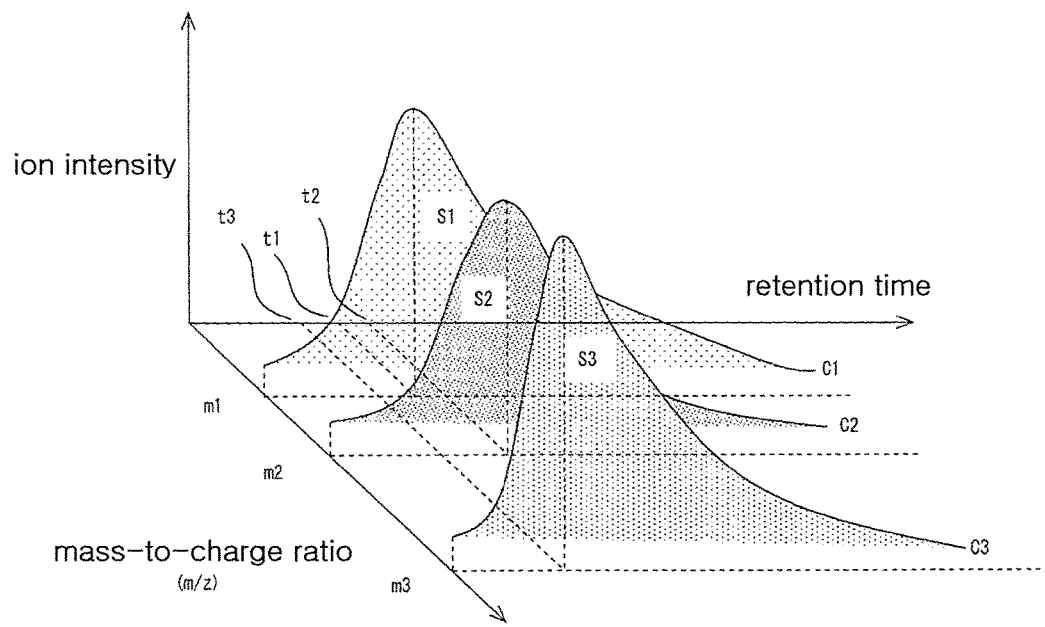
FIG. 10 is a view showing a method for analyzing evolved gas according to the exemplary embodiment of the present invention.

For example, referring to FIG. 10, chromatograms C1, C2, and C3 of the three gas components 1, 2, and 3 are obtained, and a CPU of the computer 210 calculates areas S1, S2, and S3 of the chromatograms C1, C2, and C3. In the meantime, reference areas Ss1, Ss2, and Ss3 of the gas components 1, 2, and 3 are stored in the memory unit of the computer 210. Therefore, the CPU calculates Cs of each of the gas components 1, 2, and 3 (for example, in the case of gas component 1, $Cs1=Ss1/S1$). An actual area value is calculated by multiplying Cs1 by an area of a chromatogram of the gas component 1 of the test sample. It is possible to precisely quantify the gas component 1 by using the area value.

(3) Third, a heating correction factor $H=t/ts$ is calculated by using a time t and a reference time ts indicating a maximum peak of each of the chromatograms C1, C2, and C3, the heating correction factor being used to correct a heating rate of the test sample in the heating furnace 10

(actually, on the sample plate 28 monitoring temperature). H is a heating correction factor that is used to correct a heating rate of the test sample in the heating furnace 10, when measuring the gas component of the test sample. In the case of heating the test sample, when the heating rate (temperature rising rate) varies, the shape of chromatogram (time t indicating a maximum peak) also varies, and thus, the area of the chromatogram varies. Therefore, the heating correction factor is required to be used.

For example, referring to FIG. 10, the CPU calculates times t1, t2, and t3 of the chromatograms C1, C2, and C3. In the meantime, reference times ts1, ts2, and ts3 of the gas components 1, 2, and 3 are stored in the memory unit of the computer 210. Accordingly, the CPU calculates H=t/ts of each of the gas components 1, 2, and 3.

In order to measure the chromatogram C1 of the test sample, the heating condition of the heating furnace 10 is properly controlled by using the heating correction factor H, thereby obtaining a precise chromatogram. In addition, an actual area value is calculated by multiplying the sensitivity correction factor Cs1 of the gas component 1 obtained in above (2) by an area of the chromatogram about the gas component 1 of the test sample. Therefore, it is possible to precisely quantify the gas component 1. Consequently, it is possible to correct heating performances of the heating furnace 10 or of the sample heater 27 of the evolved gas analyzer 200, measured temperature, detection sensitivity differences in analysis devices, day-to-day variations thereof, etc. by using the reference sample. In addition, a measurement accuracy (particularly, area of chromatogram) may increase.

Specifically, the heating unit heater 14a controls the temperature in the heating furnace 10 to be uniformly maintained at a certain temperature. The sample heater 27 provided under the sample plate 28 monitors the temperature of the sample using its resistance, and controls the heating rate of the sample based on the monitored temperature of the sample. Therefore, correcting the heating rate of the sample in the heating furnace means that correcting the heating rate of a part (the sample heater 27 in this example) controlling heating condition based on the temperature of the sample.

Here, when the measurement target includes a plurality of gas components, H=Σai×ti/tsi is calculated. A natural number indicating a gas component i is denoted as i, for example, gas components 1, 2, and 3. A well-known heating sensitivity factor of the gas component i is denoted as ai indicating that peak times (time t indicating a maximum peak) of the gas components easily vary depending on variations in the heating rate. According to the exemplary embodiment of the present invention, ai is heating sensitivity factors a1, a2, and a3 of the gas components 1, 2, and 3. A reference time indicating the maximum peak of the chromatogram of the gas component i is denoted as tsi. According to the exemplary embodiment of the present invention, tsi is reference times ts1, ts2, and ts3 indicating maximum peaks of the chromatograms C1, C2, and C3 of the gas components 1, 2, and 3.

Therefore, the heating correction factor is H=(a1×t1/ts1)+(a2×t2/ts2)+(a3×t3/ts3).

Figure 12:
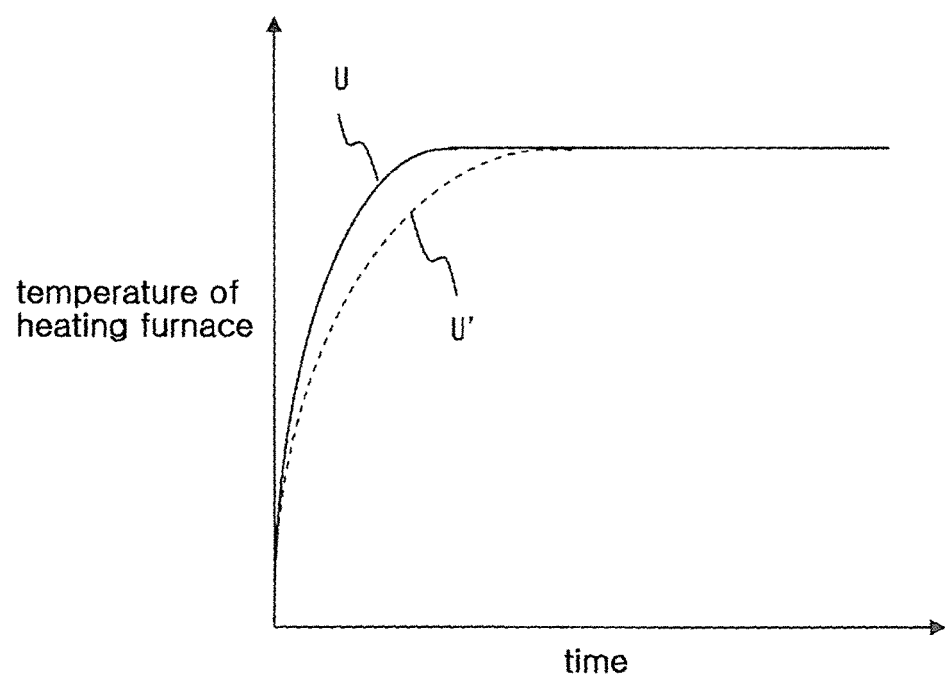
FIG. 12 is a view showing an example of correcting a heating rate of a test sample in a heating furnace by using a heating correction factor H.
Figure 13:
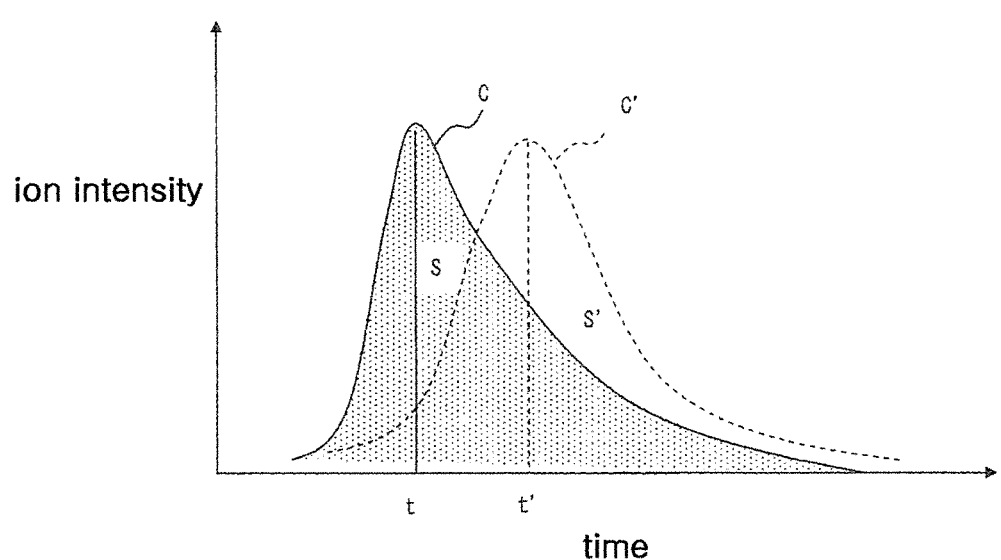
FIG. 13 is a view showing a shape change in a chromatogram caused by the heating rate of the test sample when performing mass spectrometry.

FIG. 12 is a view showing an example of correcting the heating rate of the test sample in the heating furnace 10 by using the heating correction factor H. For example, when the time t indicating maximum peak of the test sample is less than the reference time ts (H<1), the heating rate is excessive. The heating rate is required to be lower than an original heating pattern U. Therefore, the heating rate is corrected as a lower heating pattern U' by multiplying the heating correction factor H by a gradient (heating rate) of an original heating program.

Generally, when the heating rate of the sample heater 27 is too fast, gas concentration of the gas component rapidly increases. Therefore, ionizing efficiency of the ion source cannot follow the increase, and thus, a peak area value decreases. That is, it is possible to obtain a precise chromatogram by correcting the heating rate as the lower heating pattern U'.

In the case that the correction processing unit 210 automatically operates the above-described processes (1) to (3), it operates as follow.

(1) First, the detection signal determining unit 214 adjusts the settings (for example, high frequency voltage) of the mass spectrometer (quadrupole mass filter 116) 110 based on the received detection signal, in order to respectively locate the mass spectrum positions of three gas components 1, 2, and 3 within allowable ranges 2L of reference spectrum positions m1, m2, and m3 stored in the memory unit.

(2) Second, the detection signal determining unit 214 calculates the sensitivity correction factor Cs, based on the received detection signal and the reference areas Ss1, Ss2, and Ss3 stored in the memory unit. The calculated sensitivity correction factor Cs is stored in the memory unit.

(3) Third, the detection signal determining unit 214 calculates the heating correction factor H=t/ts based on the received detection signal and the reference time ts stored in the memory unit. The calculated heating correction factor H is stored in the memory unit.

Next, when performing mass spectrometry on the gas components of the test sample, the heating control device 212 corrects the heating rate of the test sample in the heating furnace 10 by controlling the sample heater 27 based on the heating correction factor H and performs measurement in this state. In addition, the detection signal determining unit 214 outputs an actual area value calculated by multiplying the sensitivity correction factor Cs1 by an area of the chromatogram of the test sample.

As described above, after the correction of the evolved gas analyzer, the mass spectrometer 110 measures a predetermined test sample, and the split ratio is determined to set the detection signal within a predetermined range. In addition, a real test sample is measured by using the split ratio.

In addition, the reference sample and the test sample are provided in an autosampler, and positions thereof are allocated. The correction process is performed based on the measurement value of the reference sample, and the split ratio is determined based on the measurement value of the test sample, and a real test sample is measured by using the split ratio.

It should be understood that the exemplary embodiment according to the concept of the present invention is not limited to the exemplary embodiment, but various modifications, equivalents, additions and substitutions are possible, without departing from the scope and spirit of the invention.

Besides phtalates, the measurement target may be brominated flame retardants (polybrominated biphenyl (PBB), polybrominated diphenyl ether (PBDE)) restricted under RoHS, without being limited thereto.

Components, shapes, configurations, etc. of the heating furnace, the sample holder, the cooling unit, the gas channel, the branching channel, the splitter, the ion source, and the mass spectrometer are not limited to the exemplary embodiments. In addition, a method of correcting the mass spectrum positions to be located at respective reference spectrum positions is not limited to the exemplary embodiment, and a conventional method may be used.

In addition, the evolved gas analyzer may be provided with an autosampler automatically continuously supplying a sample into the heating unit. The autosampler may be provided with a certain position holding the reference sample. The reference sample is analyzed once in advance of operating the method for analyzing evolved gas. Consequently, the method for analyzing evolved gas may be automatically operated.

Besides the above described rail, the sample holder supporting unit movably supporting the sample holder may be an arm, etc.

In addition, without being limited to the case that the sample holder is in direct contact with the cooling unit, a unit may be provided to be in contact with the sample holder, and the unit may be in direct contact with the cooling unit (that is, the sample holder is in indirect contact with the cooling unit).

What is claimed is:

1. A method for analyzing evolved gas using a mass spectrometer which detects a gas component evolved by heating a sample through performing mass analysis of an ion generated by ionizing the gas component, using apparatus, the method comprising:
   a discharged flow rate adjusting process, adjusting a flow rate of mixed gas of the gas component and carrier gas carrying the gas component to the mass spectrometer, discharged outside of a branching channel opened to outside, based on a detection signal received from the mass spectrometer so as to bring the detection signal within a given range wherein the branching channel is provided to a gas channel connecting a heating unit to the mass spectrometer through which the mixed gas flows, and the heating unit receives a sample holder holding the sample therein and evolves a gas component by heating the sample;
   a sample holder cooling process, cooling the sample holder by bringing the sample holder into direct or indirect contact with a cooling unit placed outside of the heating unit, when the sample holder is moved to a discharging position at which the sample can be put in and taken out; and
   a correction process, using a reference sample including the gas component as a measurement target, comprising:
   correcting a mass spectrum position to match a reference spectrum position, the mass spectrum position corresponding to a mass-to-charge ratio m/z of a mass spectrum obtained as to the gas component of the reference sample;
   after correcting the mass spectrum position, calculating a sensitivity correction factor $Cs=Ss/S$ at the time an area of a chromatogram of the gas component of the actual sample is measured, from an area S, showing an intensity with respect to a retention time obtained as to the gas component of the reference sample, and a reference area Ss; and
   calculating a heating correction factor $H=t/ts$ correcting a heating rate of the sample in the heating unit at the time the gas component of the actual sample is measured, from a time t, indicating a maximum peak of the chromatogram, and a reference time ts.

2. The method of claim 1, wherein the measurement target comprises a plurality of gas components, and the heating correction factor to be calculated is $H=\Sigma a_i \times t_i/t_{si}$ (only that, i: a natural number indicating a gas component i, $a_i$: a known heating sensitivity coefficient of the gas component i, $t_i$: a time indicating a maximum peak of a chromatogram of each gas component i, and $t_{si}$: a reference time indicating the maximum peak of the chromatogram of each gas component i).

3. The method of claim 1, wherein the discharged flow rate adjusting process is performed by measuring a given test sample after a conclusion of the correction process.

4. The method of claim 2, wherein the discharged flow rate adjusting process is performed by measuring a given test sample after a conclusion of the correction process.

5. An evolved gas analyzer comprising:
   a sample holder, holding a sample;
   a heating unit, receiving the sample holder therein, and evolving a gas component by heating the sample;
   an ion source, generating ions by ionizing the gas component evolved by the heating unit;
   a mass spectrometer, detecting the gas component by performing mass analysis of the ions;
   a gas channel connecting the heating unit to the mass spectrometer, through which mixed gas of the gas component and carrier gas, carrying the gas component to the mass spectrometer, flows, wherein the gas channel comprises a branching channel opened to outside, and the branching channel comprises a discharged flow rate adjusting device, adjusting flow rate of the mixed gas discharged to the outside;
   a flow rate control unit, controlling the discharged flow rate adjusting device based on a detection signal received from the mass spectrometer so as to bring the detection signal within a given range;
   a sample holder supporting unit movably, supporting the sample holder so as to enable moving the sample holder to given positions inside or outside of the heating unit;
   a cooling unit placed outside of the heating unit, cooling the sample holder by direct or indirect contact with the sample holder, when the sample holder is moved to a discharging position at which the sample can be put in or taken out; and
   a correction processing unit, comprising a computer including a processor and a non-transitory storage medium storing a series of executable instructions, such that when the series of executable instructions are executed, the processor performs calculations of all of the following:
   using a reference sample including the gas component as a measurement target,
   correcting a mass spectrum position to match a reference spectrum position, the mass spectrum position corresponding to a mass-to-charge ratio m/z of a mass spectrum obtained as to the gas component of the reference sample;
   after correcting the mass spectrum position, calculating a sensitivity correction factor $Cs=Ss/S$ at the time an area of a chromatogram of the gas component of the actual sample is measured, from an area S, showing an intensity with respect to a retention time obtained as to the gas component of the reference sample, and a reference area Ss; and
   calculating a heating correction factor $H=t/ts$, correcting a heating rate of the sample in the heating unit at the time the gas component of the actual sample is measured, from a time t, indicating a maximum peak of the chromatogram, and a reference time ts.

* * * * *